(12) United States Patent
Knappe et al.

(10) Patent No.: US 7,629,175 B2
(45) Date of Patent: Dec. 8, 2009

(54) TEST ELEMENT WITH A ONE LAYER REACTION FILM

(75) Inventors: Wolfgang-Reinhold Knappe, Ludwigshafen (DE); Franz Wittmann, Hockenheim (DE); Dan Mosoiu, Limbergerhof (DE); Carina Horn, Biblis (DE); Joachim Hoenes, Zwingenberg (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 717 days.

(21) Appl. No.: 11/060,956

(22) Filed: Feb. 18, 2005

(65) Prior Publication Data

US 2006/0003397 A1 Jan. 5, 2006

(30) Foreign Application Priority Data

Feb. 18, 2004 (DE) .................. 10 2004 007 983

(51) Int. Cl.
  *G01N 21/03* (2006.01)
  *G01N 21/77* (2006.01)
  *G01N 33/36* (2006.01)
  *C12Q 1/54* (2006.01)

(52) U.S. Cl. .................. 436/165; 436/95; 436/164; 436/169; 422/55; 422/56; 422/58; 422/82.05; 422/82.09; 435/14; 435/287.1

(58) Field of Classification Search .................. 436/63, 436/95, 164, 165, 169; 422/55, 56, 58, 82.05, 422/82.08, 82.09; 435/14, 287.1
  See application file for complete search history.

(56) References Cited

U.S. PATENT DOCUMENTS

| 3,802,842 | A | | 4/1974 | Lange et al. |
| 4,390,343 | A | * | 6/1983 | Walter .................. 435/7.72 |
| 4,732,849 | A | | 3/1988 | Seshimoto et al. |
| 4,935,346 | A | * | 6/1990 | Phillips et al. .................. 435/14 |
| 5,104,811 | A | * | 4/1992 | Berger et al. .................. 436/164 |
| 5,169,787 | A | * | 12/1992 | Knappe et al. .................. 436/169 |
| 5,846,837 | A | | 12/1998 | Thym et al. |
| 5,968,765 | A | * | 10/1999 | Grage et al. .................. 435/25 |
| 6,238,930 | B1 | | 5/2001 | Spichiger-Keller et al. |
| 6,455,001 | B1 | | 9/2002 | Knappe et al. |
| 2003/0031592 | A1* | | 2/2003 | Knappe .................. 422/56 |

FOREIGN PATENT DOCUMENTS

| DE | 21 18 455 A | 9/1972 |
| DE | 30 42 857 A | 5/1981 |
| EP | 0 821 233 B1 | 7/1997 |
| EP | 0 995 994 B1 | 10/1999 |
| EP | 0 960 946 A | 12/1999 |
| WO | WO 98/20348 A | 5/1998 |
| WO | WO 99/29429 | 6/1999 |
| WO | 03/097864 | * 11/2003 |

* cited by examiner

*Primary Examiner*—Maureen M Wallenhorst
(74) *Attorney, Agent, or Firm*—Bose McKinney & Evans LLP (57) ABSTRACT

The invention concerns test elements and methods for the optical detection of an analyte in a sample. The test element includes a support having at least one transparent portion, and a one-layer film positioned on the support. The film has a thickness when dry of less than about 10 μm. The method includes contacting the sample with the test element and determining the analyte concentration in the sample.

31 Claims, 6 Drawing Sheets

TEST ELEMENT WITH A ONE LAYER REACTION FILM

REFERENCE TO RELATED APPLICATIONS

The present application claims priority to German Patent Application No. 10 2004 007 983.8, filed Feb. 18, 2004 which is hereby incorporated by reference in its entirety.

TECHNICAL FIELD

The invention concerns test elements and methods for the optical detection of an analyte in a sample.

BACKGROUND

Diagnostic test elements are described in U.S. Pat. No. 3,802,842, U.S. Pat. No. 4,732,849, U.S. Pat. No. 5,846,837, and U.S. Pat. No. 6,455,001 B1, which are each hereby, incorporated by reference in their respective entirety.

SUMMARY

A test element is provided for the optical detection of an analyte. The test element comprises a support having at least one transparent portion, and a one-layer film positioned on the support, the film comprising a reagent for the detection of the analyte and having a thickness when dry about 10 μm or less.

A test element for the optical detection of an analyte is provided. The test element comprises a support having at least one transparent portion and a one-layer film positioned on the support, the film comprising a reagent for the detection of the analyte and wherein the test element is formed to determine the analyte within a reaction period of less than about 5 seconds.

A test element for the optical detection of an analyte is provided. The test element comprises a support having at least one transparent portion and a one-layer film positioned on the support, the film comprising a reagent for the detection of the analyte. The test element is formed to determine the analyte within a reaction period of less than about 5 seconds.

A test element for the optical detection of an analyte is provided. The test element comprises an at least partially optically essentially transparent support and a one-layer reaction film comprising a test reagent for determining the analyte, wherein the thickness and porosity of the reaction film and the concentration of the test reagent are adjusted such that the analyte is determined within a reaction period of less than about 5 seconds with a signal intensity that is sufficient for a quantitative determination.

A method for the detection of an analyte in a sample is provided. The method includes the steps of contacting the sample with the test element comprising a support having at least one transparent portion, and a one-layer film positioned on the support, the film comprising a reagent for the detection of the analyte and having a thickness when dry about 10 μm or less and determining the analyte concentration in the sample.

These and other features of the present invention will be more fully understood from the following detailed description of the invention taken together with the accompanying claims. It is noted that the scope of the claims is defined by the recitations therein and not by the specific discussion of the features set forth in the present description.

BRIEF DESCRIPTION OF THE DRAWINGS

The following detailed description of the embodiments of the present invention can be best understood when read in conjunction with the following drawings, where like structure is indicated with like reference numerals and in which.

Skilled artisans appreciate that elements in the figures are illustrated for simplicity and clarity and have not necessarily been drawn to scale. For example, the dimensions of some of the elements in the figures may be exaggerated relative to other elements to help improve understanding of the embodiment(s) of the present invention.

In order that the invention may be more readily understood, reference is made to the following examples, which are intended to illustrate the invention, but not limit the scope thereof.

DETAILED DESCRIPTION OF THE DRAWINGS

A test element is provided that enables a quantitative determination of analytes with a short reaction period. Test elements may be designed as strips. Test elements, however, having other forms, may be designed which for example include small quadratic or rectangular plates. The term "test element" in the following encompasses these and any additional forms.

In order that the invention may be more readily understood, reference is made to the following examples, which are intended to illustrate the invention, but not limit the scope thereof. Specifically, the following description is exemplary in nature and is in no way intended to limit the invention or its application or uses.

For the purposes of describing and defining the present invention it is noted that the term "about" is utilized herein to represent the inherent degree of uncertainty that may be attributed to any quantitative comparison, value, measurement, or other representation. The term "about" is also utilized herein to represent the degree by which a quantitative representation may very from a stated reference without resulting in a change in the basic function of the subject matter at issue.

It is noted that terms like "typically" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

A test element is provided in accordance with the present invention that allows a quantitative detection within a short reaction time. The test element includes at least one one-layer reaction film of a low thickness. For example, a reaction time of less than about 5 seconds can be obtained by using the test element having a one-layer reaction film of a low thickness. Such reaction films may also be used in combination with correspondingly adapted particle sizes of materials forming the reaction film and/or reagent concentrations in the reaction film.

The test element according to the invention is suitable for optical detection methods. Non-limiting examples of suitable detection methods include: reflection, photometric, fluorimetric, detection in the visual range of about 400 to about 800 nm, and detection in the in the ultraviolet range. In at least one embodiment of the present invention, the film has a porous structure. Moreover, the test reagent can be present in a polymer matrix.

Figure 6:
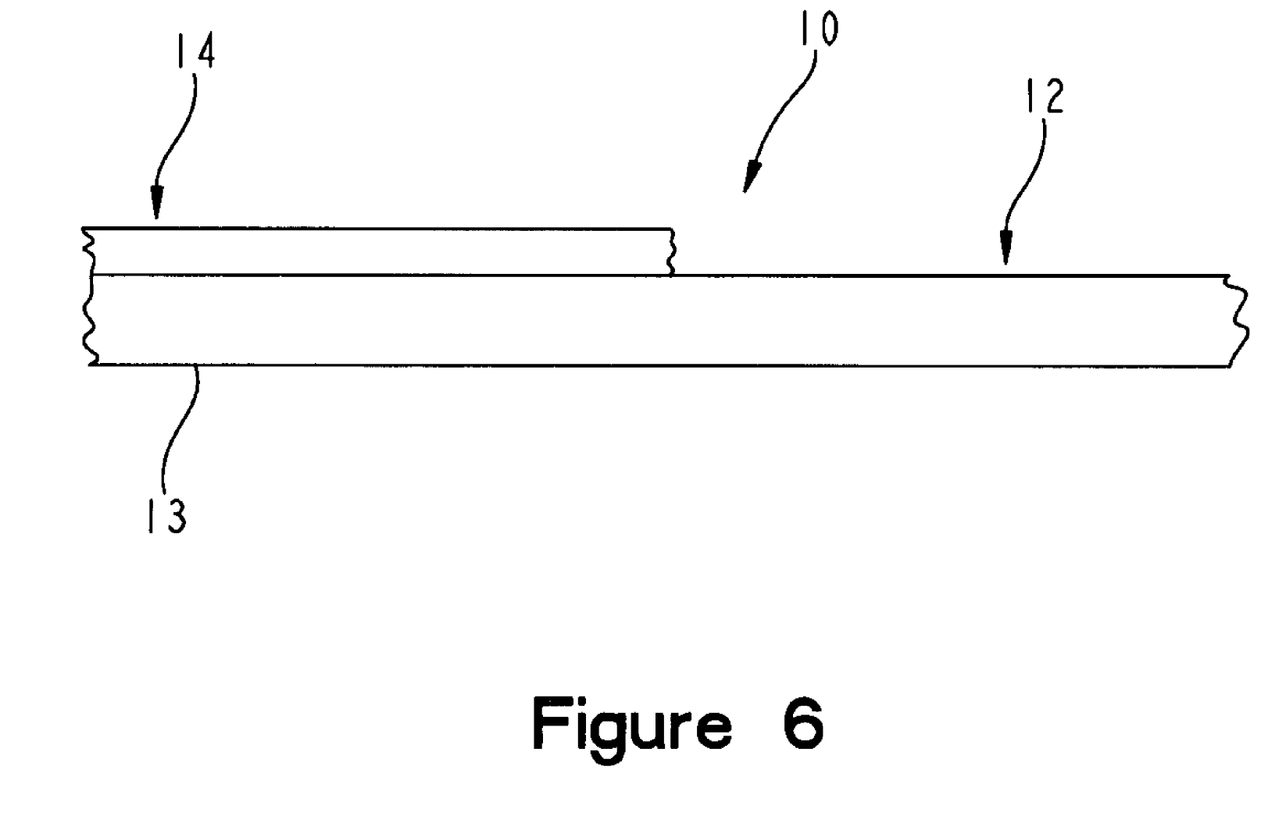
FIG. 6 shows a partial side view of a test element in accordance with the present invention.

Referring to FIG. 6, which is not drawn to scale, test element 10 according to the invention has a support 12. Support 12 is a liquid-impermeable support, non-limiting examples of which include a plastic foil such as polycarbonate, polystyrene, polyvinyl chloride, polyester or polyamide and glass. The thickness of the support is uncritical; a non-limiting example of a suitable thickness is in the range of about 10 μm to about 1 mm. Support 12 is at least partially i.e. at least in a portion used to determine the analyte (detection zone), optically essentially transparent. Referring to FIG. 6, support 12 has at least one transparent portion 13 that facilitates optical detection methods. As such, the analyte can be optically detected through the support.

Test element 10 according to the invention further includes a one-layer reaction film 14. Film 14 comprises the test reagent for determining the analyte. The one-layer reaction film is a single functional layer. The thickness of the one-layer reaction film is about 10 μm or less.

The test reagent comprises the substances required for a qualitative detection or quantitative determination of the analyte, and optionally auxiliary substances and/or additives. The test reagent comprises at least one enzyme and at least one enzyme substrate that can be directly or indirectly detected after an enzymatic reaction, non-limiting examples of which include a chromogenic or fluorescent enzyme substrate. Non-limiting example of enzymes suitable for use with the present invention are the enzymes used for detecting glucose i.e. glucose dehydrogenase e.g. glucose dehydrogenase in combination with diaphorase or PQQ-dependent glucose dehydrogenase or gluc-DOR (glucose dye oxidoreductase) and mutants thereof. The enzymes can optionally be used in a recombinant form. Such a test reagent is suitable for determining glucose in body fluids in particular for determining glucose in blood. Other non-limiting examples of suitable analytes include lactate (lactic acid), 3-hydroxybutyric acid (ketone bodies) or uric acid.

The test reagent or components thereof are present in a dry form in or on the one-layer reaction film. The test reagent can be applied to the reaction film by known methods for example by impregnation. The test element may also be present in a polymer matrix in which case the polymer is a natural or synthetic film-forming polymer. Non-limiting examples of suitable polymers include: polyvinyl ester, polyvinyl acetate, polyacrylic acid, polyacrylic ester, polyacryl amide, polymethacrylic acid, polymethacrylic ester, polyvinylamide, polyamide, polystyrene or a copolymer or mixed polymer e.g. of butadiene, styrene and maleic acid ester. The polymer can be applied to the support in a finished state or can be generated by in situ polymerization on the support in the presence of the test reagent. The reaction film can additionally comprise one or more wetting agents. Non-limiting examples of suitable wetting agents are described in U.S. Pat. No. 6,455,001 B1, which is hereby incorporated by reference in its entirety. The reaction film may include additional materials, non-limiting examples of which are: pigments and swelling agents such as xanthan gum or methyl vinyl ether maleic acid copolymer.

The concentration of the test reagent in the one-layer reaction film is adjusted such that an essentially uniform reaction with the analyte can occur over essentially the entire thickness of the reaction film. It is noted that an optimal reagent concentration is not necessarily equal to a maximum reagent concentration. A suitable reagent concentration for a given test element can be determined by determining the signal intensity as a function of the concentration of the test reagent.

Hence in one embodiment, the test element contains a concentration of the test reagent, which is adjusted by optimization of the intensity of a measuring signal. The adjustment of an optimized concentration of the test reagent is carried out at a given porosity and/or layer thickness.

The reaction film is permeable for the sample liquid. Adjusting the porosity or the particle size of the materials forming the reaction film can optimize this permeability. In one embodiment, the film is designed such that red blood corpuscles are retained on the upper side of the test element whereas dissolved sample components such as the analyte can penetrate into the reaction film. The analyte reacts with the test reagent to form an optically detectable reaction product, e.g. NADH in the case of a glucose determination. In this process a diffusion equilibrium is established between the blood retained on top of the test element and the inside of the reaction film during which the analyte e.g. glucose diffuses into the reaction film and the detectable reaction product diffuses out of the reaction film back into the sample. The concentration of the analyte can only be measured independently of time when the diffusion equilibrium is established. Consequently the porosity should be selected such that the diffusion equilibrium is achieved as rapidly as possible. Also in this case porosities can be determined by simple determinations of the signal intensity.

In another embodiment the pore size of the reaction film is adjusted by optimizing the intensity of a measuring signal. The optimization can for example be carried out under conditions in which a given concentration of the test reagent and/or a given layer thickness is used.

Overall it turns out that reagent concentration, pore size and layer thickness can be optimized for a particular application. An adaptation of the factors to one another enables adequate signal intensity.

Hence it is possible to achieve an excellent intensity of the measuring signals using a one-layer reaction film with a thickness of 10 μm (dry) or less. Further, the one-layer reaction film may have a thickness in the range of about 2 μm to about 10 μm (dry). Still further, the one-layer reaction film may have a thickness in the range of about 5 μm to about 8 μm (dry). As a result the analyte can be quantitatively determined within a reaction period of less than about 5 seconds. Further, the analyte can be quantitatively determined within a reaction period of about 1 second to about 4 seconds. Still further, the analyte can be quantitatively determined within a reaction period of about 1 second to about 2 seconds.

In an embodiment of the invention, the test element is designed for the reflection photometric detection of an analyte. In this embodiment, the one-layer reaction film contains fine-grained pigment particles, for example pigment particles based on $TiO_2$ and/or $ZrO_2$. The average diameter of the fine-grained pigment particles, which result in an optical reflection of the measuring signal towards a detector and thus increase the signal intensity, is less than about 0.5 μm. Further, the average diameter of the particles may be about 0.1 μm to about 0.3 μm. Still further, the average diameter of the particles may be about 0.2 μm which is typically present in commercial titanium dioxide pigments e.g. type RN 56 or E 171 from the Kronos Company, Leverkusen, Germany.

In the above embodiment of the test element, the one-layer reaction film additionally comprises medium-grained and/or coarse-grained particles. These particles are: (i) medium-grained and/or coarse-grained pigment particles for example pigment particles based on $TiO_2$ and/or $BaSO_4$, and/or (ii) medium- and/or coarse-grained particles of a non-reflecting filler for example $SiO_2$ and/or a silicate and/or a water-insoluble plastic.

Non-limiting examples of medium- and/or coarse-grained pigment particles include: $TiO_2$, $BaTiO_3$, $ZrO_2$, $ZrSiO_3$ and/or $BaSO_4$. Non-limiting examples of the medium- and/or coarse-grained particles of a non-reflecting filler include: $SiO_2$ (e.g. precipitated silicic acid FK 320 from Degussa Corporation, Parsippany, N.J.), silicates (e.g. transpafill from Degussa Corporation, Parsippany, N.J.) or insoluble organic plastics (e.g. cross-linked polyvinyl pyrrolidone such as KOLLIDON® CL-M, BASF Co., Ludwigshafen). The average diameter of medium-grained particles is about 0.7 µm to about 4 µm. Further, the average diameter of medium-grained particles is about 1 µm to about 3 µm. The average diameter of coarse-grained particles is at least about 4 µm. Further, the average diameter of coarse-grained particles is about 4 µm to about 8 µm.

In one embodiment the reaction film of the test element comprises a mixture of fine-grained pigment particles and coarse-grained particles. Further, the test element comprises a mixture of fine-grained pigment particles and coarse-grained particles in a weight ratio of about 1 (fine-grained pigment particles):0.2 (coarse-grained particles) to about 1 (fine-grained pigment particles):1 (coarse-grained particles)

In another embodiment the one-layer reaction film of the test element comprises a mixture of fine-grained pigment particles and medium-grained particles. Further, the test element comprises a mixture of fine-grained pigment particles and medium-grained particles a weight ratio of about 1 (fine-grained particle):0.2 (medium-grained particle) to about 1 (fine-grained particle):1 (medium-grained particle).

In yet another embodiment the test element comprises a mixture of fine-grained pigment particles and coarse-grained particles and medium-grained particles. Further, the test element comprises a mixture of fine-grained pigment particles and coarse-grained particles and medium-grained particles in a weight ratio of about 1 (fine-grained particles):0.1-0.9 (coarse-grained particles):0.1-0.9 (medium-grained particles).

In particular when $ZrO_2$ is used as the pigment and the above-mentioned medium-grained and/or coarse-grained particles are used, test elements according to the invention are obtained which are suitable for a photometric detection in the UV range e.g. for detecting NADH at about 340 to about 370 nm in reflection photometric methods as well as in fluorimetric methods.

In the fluorimetric detection of analytes, it is not necessary to use a reaction film that comprises pigments. However, it turns out that also in this case the measurement time and signal intensity can be optimized by the layer thickness, reagent concentration and porosity of the film.

The one-layer reaction film can be applied to the support by known methods. In one embodiment the coating compound required for the one-layer reaction film is applied to the support in the desired layer thickness, non-limiting examples of which include by pouring, by spreading using brushes or spreading knives or by roller application or by a combination of these methods, and dried. The reaction film can then be fixed on the support also by known methods, non-limiting examples of which include by adhesion foils or adhesive tapes.

In addition to the support and one-layer reaction film, the test element can comprise other components. Thus a spreading overlay may be present on the reaction film. Such a spreading layer supplies sample liquid uniformly and rapidly to the reaction film or uniformly distributes the sample liquid over several adjacent reaction films on the support. Optionally the spreading overlay may also have the function of leading excess analyte sample away from the test element.

The test element can additionally comprise an application area for sample material e.g. a capillary gap or a capillary channel, which is used to transport liquid from the sample application area of the test element to a detection zone on the one-layer reaction film. In addition protective covers, spacers, adhesion layers and observation and measurement openings may be present. With regard to the construction of suitable test elements reference is made among others to U.S. Pat. No. 6,455,001 B1 and U.S. Pat. No. 7,008,799 to Zimmer, filed on May 19, 2000, each of which is hereby incorporated by reference in their entirety.

The method according to the invention for detecting an analyte comprises contacting the test element according to the invention with a sample and qualitatively detecting or quantitatively determining the analyte concentration in the sample. The quantitative determination is carried out by optical methods, non-limiting examples of which include by reflection photometric and fluorimetric detection. Furthermore the quantitative determination takes place within a reaction period of less than about 5 seconds. Further, the quantitative determination takes place within a reaction period of about 1 second to about 4 seconds. Still further, the quantitative determination takes place within a reaction period of about 2 seconds.

In order to carry out the method, the sample liquid is applied to the test element such that the liquid saturates the reaction film. When a spreading overlay is used, the sample liquid is applied, for example, to the side of a spreading overlay facing away from the reaction film, in which case so much sample liquid is applied that the liquid passing through the spreading overlay saturates the reaction film. Non-limiting examples of suitable sample liquids include body fluids such as blood, plasma, serum, urine, saliva etc. In one embodiment, blood or liquids derived from blood such as plasma or serum as well as urine are suitable sample liquids.

In one embodiment, as a result of the reaction that takes place in the reaction film between the test reagent and analyte, a measuring signal is generated which correlates with the concentration of the analyte in the sample liquid. This measuring signal is a change in color, which is understood to include color formation, loss of color or change in color. This color change is quantitatively evaluated by visual means or with the aid of an instrument, by reflection photometry for which appropriate detectors can be used. Alternatively the software of the measuring device can directly display the analyte content. In another one embodiment the signal is a fluorescence, which occurs by irradiating the test element with light of an excitation wavelength and detecting the light emitted from the sample at an emission wavelength.

It is intended to further elucidate the present application by the following examples:

EXAMPLE 1

Test Element for the Reflection Photometric Determination of Glucose with PQQ-Dependent Glucose Dehydrogenase The coating compound was mixed by stirring the following components—as a pure substance or in the form of stock solutions—in a beaker:

| | |
|---|---|
| water | 80.50 g |
| methyl vinyl ether-maleic acid copolymer | 1.36 g |
| sodium hydroxide | 0.49 g |
| tetraethylammonium chloride | 0.68 g |
| N-octanoyl-N-methyl-glucamide | 0.34 g |
| sodium N-methyl-N-oleoyl-taurate | 0.03 g |
| precipitated silicic acid FK 320 DS (Degussa Corporation, average diameter 5 µm) | 6.03 g |
| titanium dioxide E 171 (Kronos Company, average diameter 0.2 µm) | 14.44 g |
| polyvinyl propionate dispersion (50% by weight in water) | 5.77 g |
| N,N-bis-(2-hydroxyethyl)-4-nitroso-aniline hydrochloride | 0.30 g |
| 2,18-phosphomolybdic acid hexasodium salt | 2.22 g |
| pyrroloquinoline quinone | 0.0032 g |
| calcium chloride-2-hydrate | 0.05 g |
| glucose dehydrogenase rec from Acinetobacter calcoaceticus EC 1.1.99.17 | 0.26 g (=180 kU) |
| 1-hexanol | 0.16 g |
| 1-methoxy-2-propanol | 4.26 g |
| potassium hexacyanoferrate (III) | 0.01 g |

The total mixture was adjusted with NaOH to a pH of 6.8 and then applied with a spreading gap of 30 µm height to a 125 µm thick polycarbonate foil and dried.

A 5 mm wide strip of the reaction film prepared in this manner was glued with its foil side to a punched double-sided adhesive tape on the support layer so that it fit. Double-sided adhesive tapes were glued onto the support as spacers directly adjacent to the reaction film and on both sides. Afterwards the protective foil of the double-sided adhesive tapes was removed. A 20 mm wide strip of a spreading fleece prepared according to U.S. Pat. No. 6,455,001 B1, the specification of which is hereby incorporated by reference, was placed on this composite and glued by pressing. Two single-sided adhesive tapes were glued as covers onto the spreading fleece in such a manner that the spacers were covered and there was still at least a slight overlap with the reaction film. The tape material finished in this manner was cut into 6 mm wide test elements so that the measurement hole was in the middle of the test element.

The following description of the one embodiment is merely exemplary in nature and is in no way intended to limit the invention or its application or uses.

Figure 1:
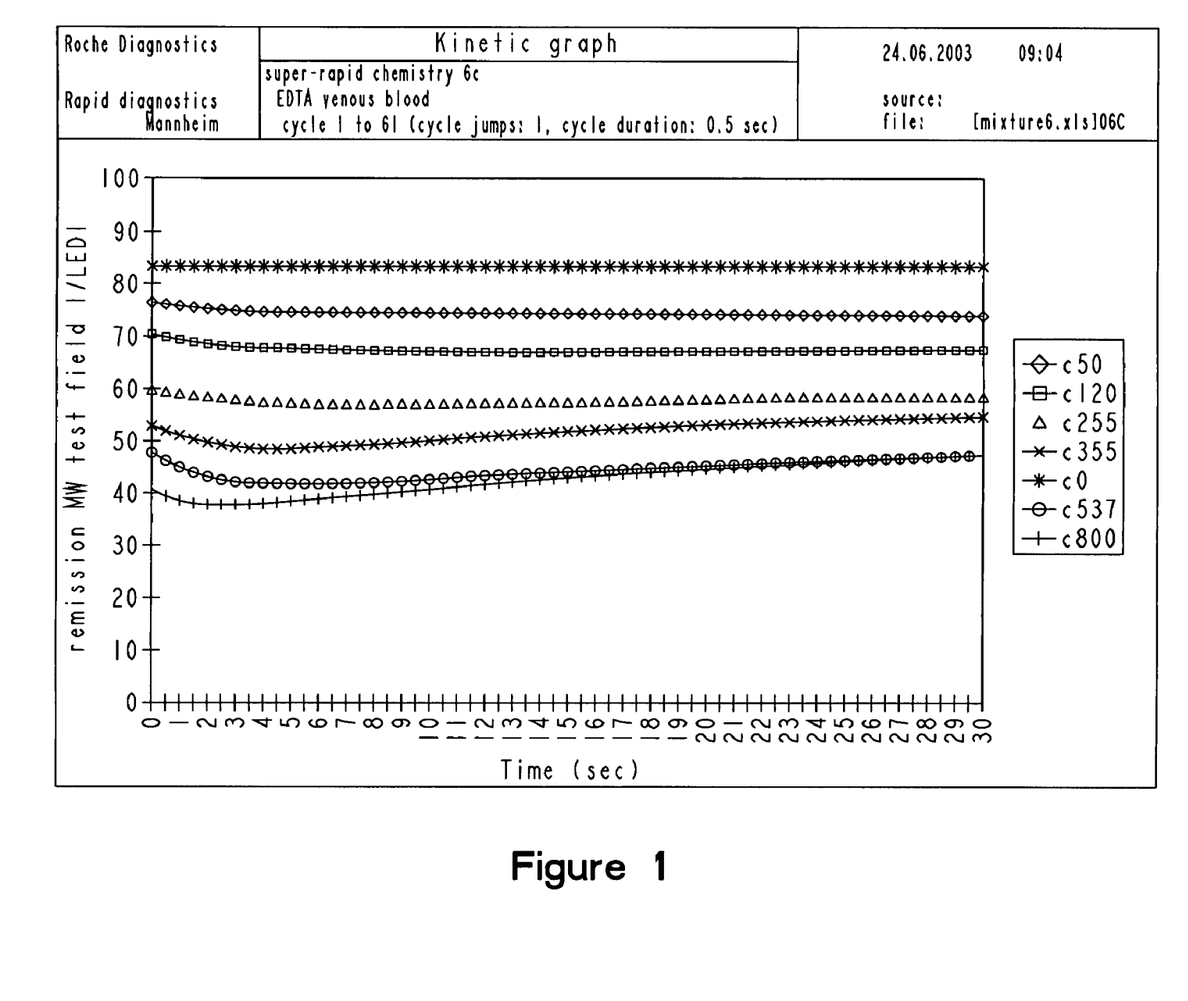
FIG. 1 illustrates time courses of color development of a reaction film in accordance with an embodiment of the present invention.

The test elements were measured using various glucose concentrations in EDTA venous blood on PC-controlled ACCUCHECK® Active instruments, Roche Diagnostics GmbH, Mannheim Germany. The time courses of color development that were obtained are shown in FIG. 1. Due to the software that was used the first three measurement cycles at 0.5 second intervals are not included in the Filigree 1.

It was found that a one layer film of about 7 µm thickness (dry) pigmented with TiO₂ yielded a measuring signal of ca. 45% remission (absolute) for the measuring range of 10-600 mg/dl glucose. The reaction time is about 1-2 seconds.

EXAMPLE 2

Test Element for the Reflection Photometric Determination of Glucose with glucDOR A test element was prepared according to the method described in Example 1 in which glucDOR (wild type) was used instead of glucose dehydrogenase. The fine-grained pigment (titanium dioxide, average diameter 0.2 µm) was diluted as follows with medium- or coarse-grained particles:

(a) pigment and coarse-grained filler e.g. 14 g TiO₂ (0.2 µm particle size, narrow distribution)+6 g SiO₂ (5 µm, wide distribution) were mixed.

(b) pigment and medium-grained filler e.g. 14 g TiO₂ (0.2 µm particle size)+6 g TiO₂ (2-3 µm, medium distribution) or BaSO₄ (1 µm, medium distribution) were mixed.

(c) pigment and medium-grained filler e.g. 9 g TiO₂ (0.2 µm particle size)+4.5 g BaSO₄ (1 µm)+4.5 g SiO₂ (5 µm) were mixed.

The solids contents of the coating compound were kept almost constant in this process.

Figure 2:
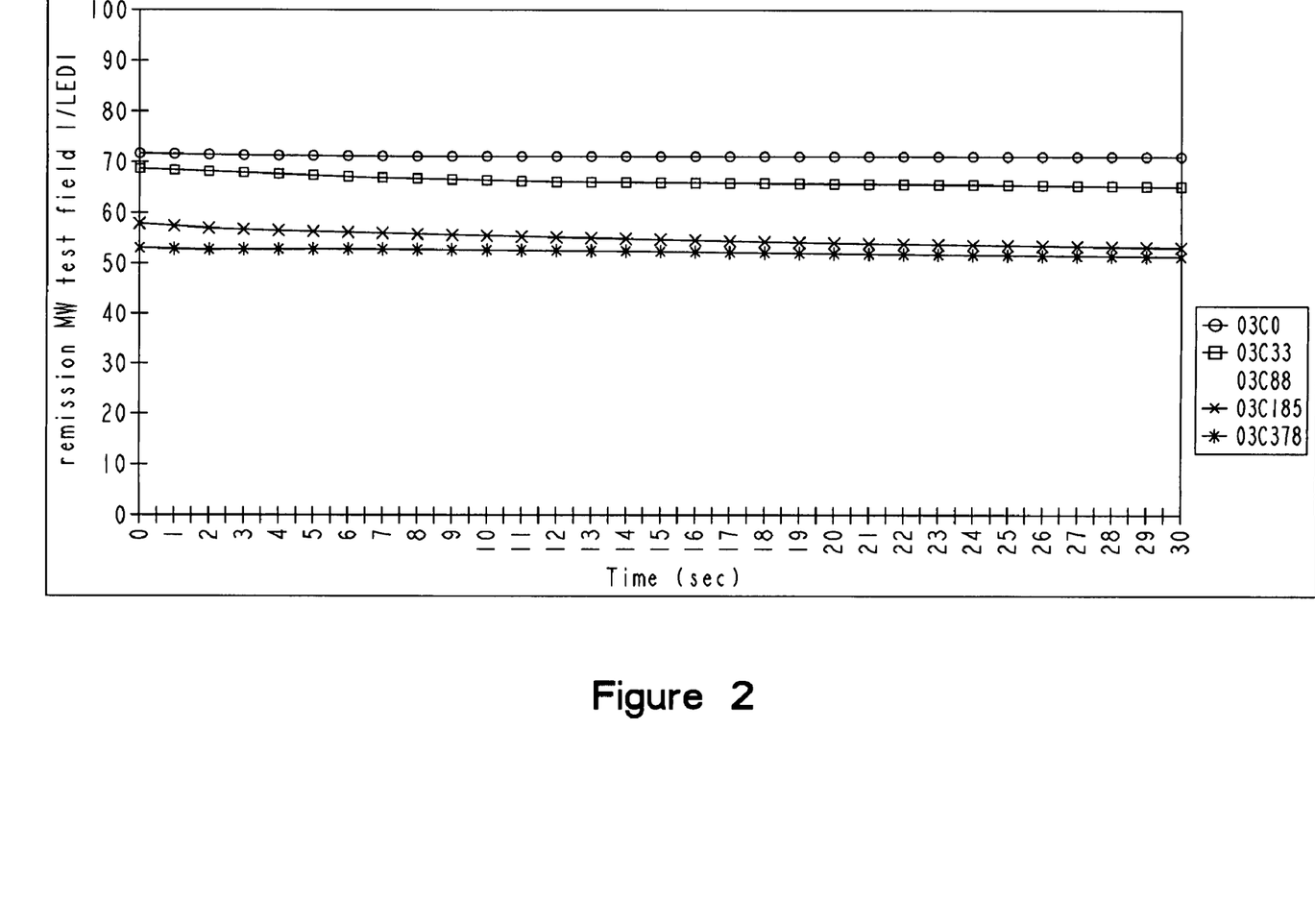
FIG. 2 illustrates measurement results for a determination of glucose in EDTA venous.
Figure 3:
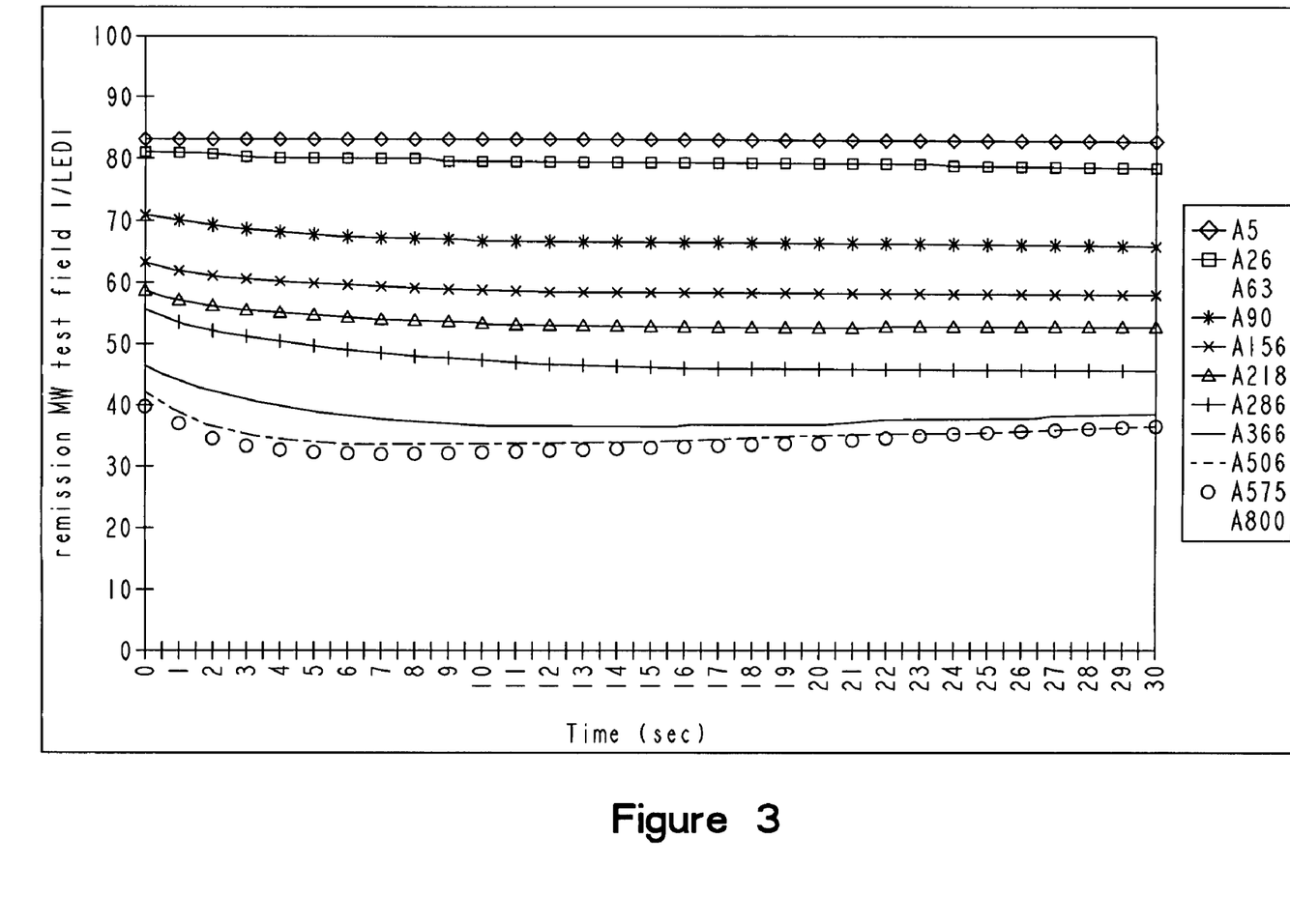
FIG. 3 illustrates measurement results for a determination of glucose in EDTA venous.
Figure 4:
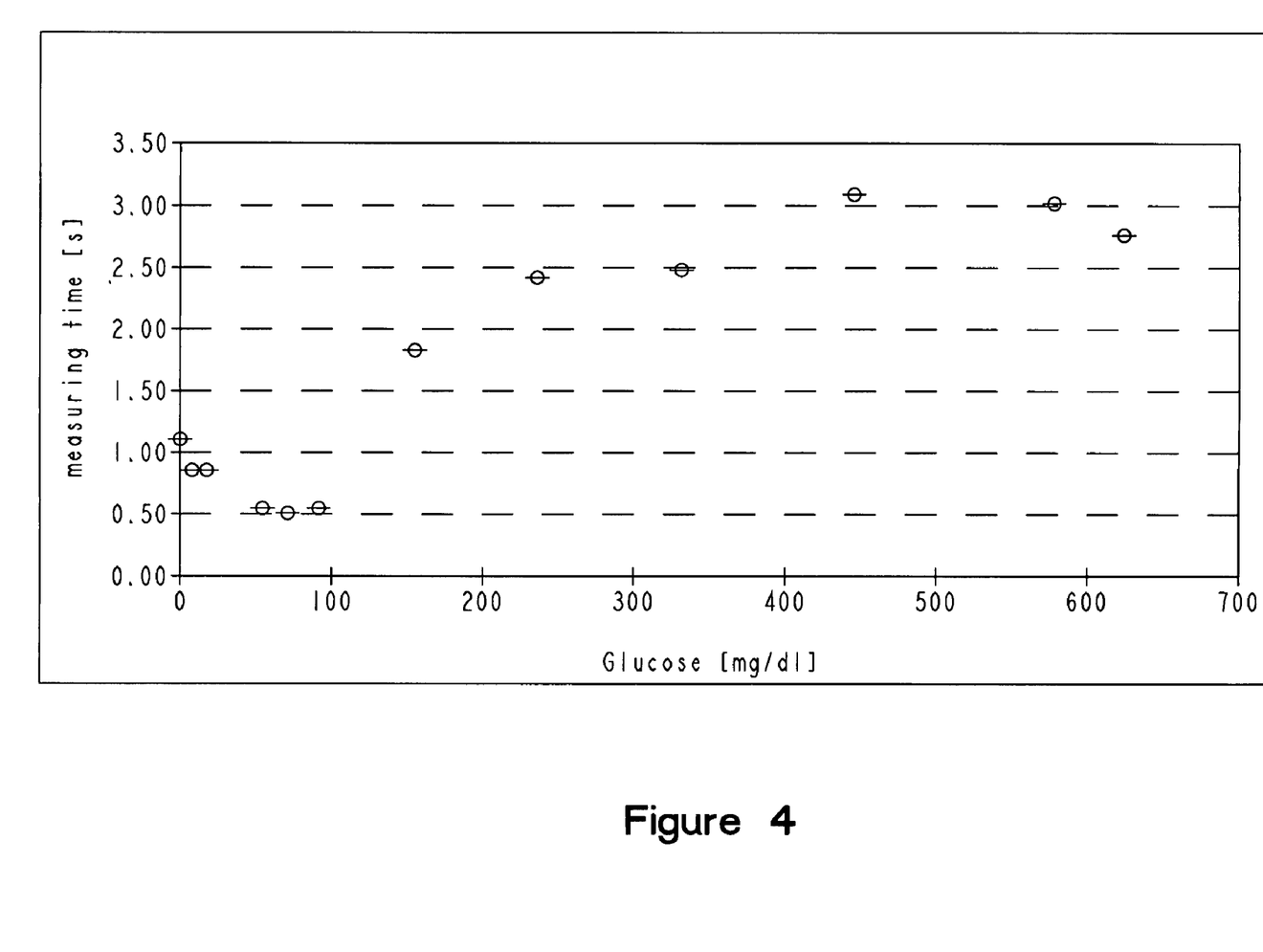
FIG. 4 illustrates measurement results for a determination of glucose in EDTA venous.

The measurement results for a determination of glucose in EDTA venous blood are shown in FIG. 2 for preparation (a), in FIG. 3 for preparation (b) and in FIG. 4 for preparation (c).

EXAMPLE 3

Test Element for the Fluorimetric Detection of Glucose with Glucose Dehydrogenase (glucDH)

A polymerization and impregnation solution comprising the following components was prepared:

| | solution |
|---|---|
| Polymerization | |
| glucDH (50% NaCl) | 27 U/mg 5.8 g |
| buffer pH 7.0, FLUKA | 20.3 g |
| NAD⁺, free acid | 0.9 g |
| buffer (FLUKA) pH 7 | 10.04 g |
| ethanol | 8.3 g |
| N-acryloyl-trishydroxymethyl aminomethane | 2.1 g |
| poly-(vinylsulfonic acid) sodium salt | 2.1 g |
| initiator | 2.1 g |
| pH value | 8.30 |
| pH, adjusted with HCl | 6.02 |
| Impregnation | |
| benzophenone (5%) | 2.00 g |
| acetone | 4.00 g |
| ethanol | 4.00 g |
| | 10.00 g |

A POKALON® foil (140 µm) (LOFO High Tech Film GmbH, Weil am Rhein Germany) was coated with the impregnation solution using a spreading system (10 µm wet layer) and subsequently dried in a drying oven at 50° C. for 15-20 min.

Subsequently the polymerization solution was added to a plastic saucer and the preimpregnated foil is placed on top. The mixture was polymerized onto the foil through the foils with the aid of a lamp (Fluotest Forte, mercury vapour lamp, no filter, wavelength 280 nm-360 nm). The supernatant was washed with water and subsequently the polymerized film was dried for 15 minutes in a drying cabinet at 50° C.

Figure 5:
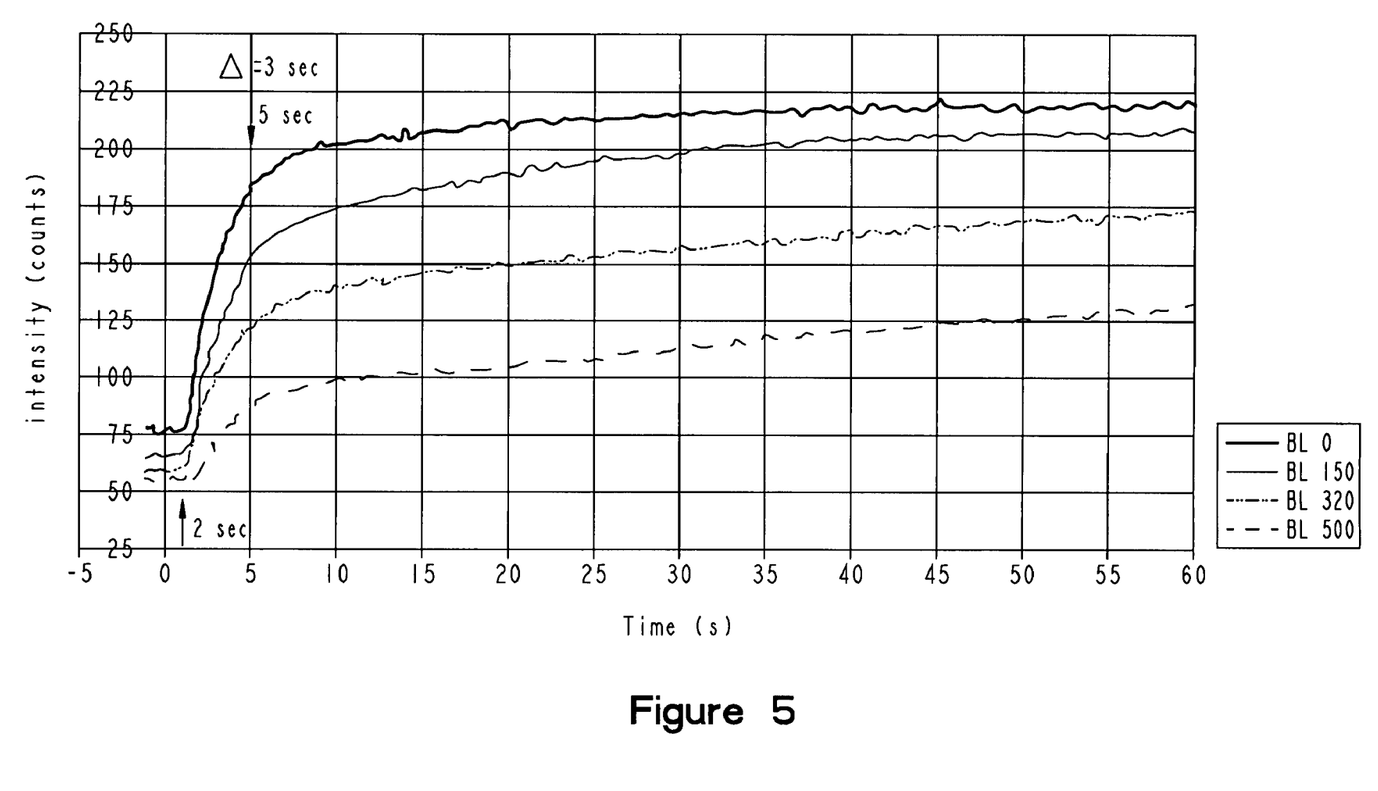
FIG. 5 shows measurement results for a determination of glucose.

FIG. 5 shows the accompanying blood measurement. The initial values show the dry value of the test element, the welting takes place within about 2 seconds. The plateau is reached at about 5 seconds so that a measuring time of about 3 seconds is sufficient.

Having described the invention in detail and by reference to specific embodiments thereof, it will be apparent that modification and variations are possible without departing from the scope of the invention defined in the appended claims. More specifically, although some aspects of the present invention are identified herein, it is contemplated that the present invention is not necessarily limed to these one aspects of the invention.

What is claimed is:

1. A test element for the optical detection of an analyte comprising:
    a support having at least one transparent portion, and
    a one-layer film positioned on the support, the film comprising a reagent for the reflection photometric detection of the analyte and pigment particles, the film having a thickness when dry about 10 µm or less, wherein the test element comprises only one functional layer, and wherein the film comprises a mixture of fine-grained pigment particles having an average diameter of less than 0.5 µm with medium and/or coarse-grained particles, the average diameter of medium grain particles being between about 0.7 µm and about 4 µm and the average diameter of coarse-grained particles being between about 4 µm and about 8 µm.

2. The test element of claim 1 wherein the thickness of the film when dry is about 2 µm to about 10 µm.

3. The test element of claim 1 wherein the reagent comprises at least one enzyme and at least one enzyme substrate that can be detected after an enzymatic reaction with the analyte.

4. The test element of claim 1 wherein a concentration of the reagent in the film is such that the test element supports a generally uniform reaction with the analyte over the thickness of the test element.

5. The test element of claim 1 wherein the film is porous.

6. The test element of claim 5 wherein the pore size is such that penetration of erythrocytes into the film is generally excluded.

7. The test element of claim 1 wherein the support comprises a liquid-impermeable support.

8. The test element of claim 1 wherein the pigment particles are based on $TiO_2$.

9. The test element of claim 1 wherein the pigment particles are based on $ZrO_2$.

10. The test element of claim 1 wherein the average diameter of the fine-grained pigment particles is between about 0.1 µm and about 0.3 µm.

11. The test element of claim 1 wherein the medium or coarse grained particles are selected from the group consisting of $TiO_2$, $BaTiO_3$, $ZrO_2$, $ZrSiO_3$ and $BaSO_4$.

12. The test element of claim 1 wherein the medium-grained or coarse-grained particles are selected from the group consisting of $SiO_2$, a silicate, and a water-insoluble plastic.

13. The test element of claim 1 wherein the average diameter of the medium-grained particles is between about 1 µm and about 3 µm.

14. The test element of claim 1 wherein the mixture of fine-grained pigment particles and coarse-grained particles has a weight ratio of about 1:0.2 to about 1:1.

15. The test element of claim 1 wherein the mixture of fine-grained pigment particles and medium-grained particles has a weight ratio of about 1:0.2 to about 1:1.

16. The test element of claim 1 wherein the mixture of fine-grained pigment particles, coarse-grained particles and medium-grained particles has a weight ratio of about 1:0.1:0.9.

17. The test element of claim 1 wherein the reagent is present in a polymer matrix.

18. The test element of claim 1 wherein the reagent is formed for the detection of NADH.

19. The test element of claim 1 wherein the reagent is formed for the visible detection an analyte.

20. The test element of claim 1 wherein a reaction period for the detection of the analyte is less than about 5 seconds.

21. The test element of claim 1 wherein a reaction period for the detection of the analyte is about 1 second to about 4 seconds.

22. The test element of claim 1 wherein a reaction period for the detection of the analyte is about 2 seconds.

23. A test element for the optical detection of an analyte comprising:
    a support having at least one transparent portion, and
    a one-layer film positioned on the support, the film comprising a reagent for the reflection photometric detection of the analyte and pigment particles, wherein the test element is formed to determine the analyte within a reaction period of less than about 5 seconds, and wherein the test element comprises only one functional layer, and wherein the film comprises a mixture of fine-grained pigment particles having an average diameter of less than 0.5 µm with medium and/or coarse-grained particles, the average diameter of medium grain particles being between about 0.7 µm and about 4 µm and the average diameter of coarse-grained particles being between about 4 µm and about 8 µm.

24. A test element for the optical detection of an analyte comprising:
    an at least partially optically essentially transparent support and
    a one-layer reaction film positioned on the support and comprising a test reagent for the reflection photometric determination of the analyte and pigment particles, wherein the thickness and porosity of the reaction film and the concentration of the test reagent are adjusted such that the analyte is determined within a reaction period of less than about 5 seconds with a signal intensity that is sufficient for a quantitative determination, and wherein the test element comprises only one functional layer, and wherein the film comprises a mixture of fine-grained pigment particles having an average diameter of less than 0.5 µm with medium and/or coarse-grained particles, the average diameter of medium grain particles being between about 0.7 µm and about 4 µm and the average diameter of coarse-grained particles being between about 4 µm and about 8 µm.

25. The test element of claim 24 wherein the reaction period is about 1 to about 4 seconds.

26. The test element of claim 24 wherein the reagent is suitable for the determination of an analyte selected from the group consisting of: glucose, lactate, ketone bodies and urea.

27. The test element of claim 24, wherein the test reagent comprises an enzyme system selected from the group consisting essentially of: glucose dye oxidoreductase and glucose dehydrogenase.

28. A method for the detection of an analyte in a sample comprising the steps:
    contacting the sample with a test element comprising a support having at least one transparent portion, and a one-layer film positioned on the support, the film comprising a reagent for the reflection photometric detection of the analyte and pigment particles, the film having a thickness when dry about 10 µm or less and wherein the test element comprises only one functional layer, and wherein the film comprises a mixture of fine-grained pigment particles having an average diameter of less than 0.5 µm with medium and/or coarse-grained particles, the average diameter of medium grain particles being between about 0.7 µm and about 4 µm and the average diameter of coarse-grained particles being between about 4 µm and about 8 µm; and determining the analyte concentration in the sample using reflection photometry of the test element.

29. The method of claim 28 wherein the determination takes place within a reaction period of less than about 5 seconds.

30. The method of claim 28 wherein the determination takes place within a reaction period of about 1 to about 4 seconds.

31. The method of claim 28 wherein the analyte is glucose.

* * * * *

UNITED STATES PATENT AND TRADEMARK OFFICE
CERTIFICATE OF CORRECTION

PATENT NO.       : 7,629,175 B2                                    Page 1 of 1
APPLICATION NO.  : 11/060956
DATED            : December 8, 2009
INVENTOR(S)      : Knappe et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 961 days.

Signed and Sealed this

Twenty-first Day of December, 2010

David J. Kappos
*Director of the United States Patent and Trademark Office*